United States Patent [19]

Hodakowski et al.

[11] Patent Number: 4,479,946

[45] Date of Patent: Oct. 30, 1984

[54] PHOSPHORUS ESTERS OF AMIDOXIMES, AND COMPOSITIONS FOR AND METHODS OF CONTROLLING INSECTS USING THEM

[75] Inventors: Leonard E. Hodakowski, St. Albans; Dean F. Bushey, South Charleston, both of W. Va.

[73] Assignee: Union Carbide Corporation, Danbury, Conn.

[21] Appl. No.: 378,852

[22] Filed: Jun. 17, 1982

Related U.S. Application Data

[63] Continuation of Ser. No. 163,495, Jun. 27, 1980, abandoned.

[51] Int. Cl.³ .......................... A01N 57/32; C07F 9/65
[52] U.S. Cl. ...................................... 424/200; 544/10; 544/14; 544/57; 544/214; 544/244; 548/113; 548/119; 260/245.5
[58] Field of Search .................. 544/244, 214, 10, 14, 544/57, 67; 548/113, 119; 260/245.5; 424/200

[56] References Cited

U.S. PATENT DOCUMENTS

| | | | |
|---|---|---|---|
| 3,717,690 | 2/1973 | Newman | 260/945 |
| 3,900,499 | 8/1975 | Hörlein et al. | 424/202 X |
| 3,904,759 | 9/1975 | Punja | 424/270 |
| 3,930,002 | 12/1975 | Durden, Jr. | 424/246 |
| 3,949,023 | 4/1976 | Sasaki et al. | 260/944 |
| 3,966,953 | 6/1976 | D'Silva | 424/270 |
| 4,339,444 | 7/1982 | D'Silva et al. | 424/202 |

FOREIGN PATENT DOCUMENTS 2131745  12/1971  Fed. Rep. of Germany .

OTHER PUBLICATIONS

Oglobin, et al., J. Gen. Chem. USSR, vol. 34, pp. 1225–1231 (1964).

*Primary Examiner*—Nicholas S. Rizzo
*Assistant Examiner*—Diana G. Rivers
*Attorney, Agent, or Firm*—Clement J. Vicari

[57] ABSTRACT

Novel phosphorus esters of amidoximes and methods of preparing same. This invention is also directed to pesticidal compositions comprising an acceptable carrier and a pesticidally effective amount of a compound of this invention, as well as to a method of controlling pests which comprises subjecting the pests to a pesticidally effective amount of a compound of this invention.

27 Claims, No Drawings

PHOSPHORUS ESTERS OF AMIDOXIMES, AND COMPOSITIONS FOR AND METHODS OF CONTROLLING INSECTS USING THEM

This application is a continuation of our prior U.S. application; Ser. No. 163,495, filing date June 27, 1980, now abandoned.

This invention relates to novel phosphorus esters of amidoximes and methods of preparing same. This invention is also directed to pesticidal compositions comprising an acceptable carrier and a pesticidally effective amount of a compound of this invention, as well as to a method of controlling pests which comprises subjecting the pests to a pesticidally effective amount of a compound of this invention.

More particularly, this invention relates to compounds of the formula:

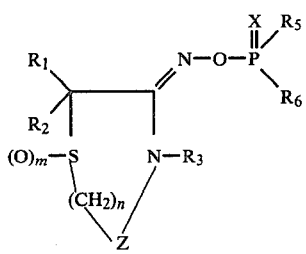

wherein
m is 0, 1 or 2
n=0 or 1;
X=O or S;
$R_1$ and $R_2$ can be the same or different and are hydrogen or $C_1-C_6$ alkyl; with the proviso that when n is 0, Z is C=N—$R_4$, and when n is 1, Z is $CH_2$ and $R_3$ is hydrogen or lower alkyl;
$R_3$ and $R_4$ can be the same or different and is lower alkyl ($C_1-C_6$) or together forms a cyclic or bicyclic alkylene, alkenylene, or an ortho-substituted phenylene group thereby forming an unsaturated five, six or seven membered heterocyclic ring which can also contain oxygen, sulfur, nitrogen, or carbonyl, said alkylene alkenylene, or phenylene ring systems being optionally substituted with one or more $C_1-C_4$ alkyl, alkoxy, phenoxy, alkylthio, halogen, amido, alkylamido, nitrile, acyl, or nitro group with any ring sulfurs being present in any of their oxidation states; $R_5$ and $R_6$ is the same or different and is $C_1-C_5$ alkyl, $C_1-C_5$ alkoxy, $C_1-C_5$ alkylthio, alkylthioalkyl, dialkylamino, or alkylimino.

All compounds within the purview of the above generic formula exhibit pesticidal activity to a lesser or greater extent. Some of these compounds exhibit very powerful pesticidal activity in extremely small dosages while others require larger dosages to be pesticidally effective.

Preferred because of their higher level of pesticidal activity are the compounds of this invention in which:
m is 0,
n is 0,
x is Oxygen, or sulfur
Z is C=N—$R_4$
$R_1$ and $R_2$ is $CH_3$, and
$R_3$ and $R_4$ are both lower alkyl and particularly $CH_3$, —$CH_2CH_3$, ISO-$C_3H_7$ or taken together to form a five or six saturated or unsaturated ring.

The following pesticidally active compounds are illustrative of compounds within the purview of the above generic formula and which can be conveniently prepared by the process of this invention simply by selecting appropriate reactants for use in the procedures described below.

2,2,5,5,8,8-Hexamethyl-3-[((ethoxy)(propylthio)phosphinothioyl)oximino]-2,3,5,6,7,8-hexahydrothiazolo[3,2-a][1,3]diazepine.

2,2-Dimethyl-3-[((ethoxy)(propylthio)phosphinothioyl)oximino]-2,3-dihydrothiazolo[3,2-a]benzimidazole.

6,6-Dimethyl-5-[((ethoxy)(propylthio)phosphinothioyl)oximino]-5,6-dihydrothiazolo[2,3-c]1,2,4-triazole.

2,2-Dimethyl-6N-cyclohexyl-3-[((ethoxy)(propythio)phosphinothioyl)oximino]-2,3,5,6-tetrahydro-7H-thiazolo[3,2-a]triazine.

2,2-Dimethyl-3-[((ethoxy)(propylthio)phosphinothioyl)oximino]-7-oxo-2,3-dihydro-7H-thiazolo[3,2-a]pyrimidine.

2,2-Dimethyl-3-[((ethoxy)(propylthio)phosphinothioyl)oximino]-2,3,4,5,6,7-hexahydrothiazolo[3,2-c][1,3,5]thiadiazine.

2,2-Dimethyl-3-[((ethoxy)(propylthio)phosphinothioyl)oximino]-2,3-dihydro-9H-thiazolo[3,2-a]quinazoline.

5,6-Dichloro-2,2-dimethyl-3-[((ethoxy)(propylthio)phosphinothioyl)oximino]-2,3-dihydroimidazo[2,1-b]thiazole.

5,6-Dicyano-2,2-dimethyl-3-[((ethoxy)propylthio)phosphinothioyl)oximino]-2,3-dihydroimidazo[2,1-b]thiazole.

2,2-Dimethyl-3-[((ethoxy)(propylthio)phosphinothioyl)oximino]-5-oxo-2,3-dihydro-5H-thiazolo[3,2-a]pyrimidine.

5,5-Dimethyl-6-[((ethoxy)(propylthio)phosphinothioyl)oximino]-2,3-dihydrothiazolo[3,2-d]tetrazole.

2,2-Dimethyl-3-[((ethoxy)(propylthio)phosphinothioyl)oximino]-2,3,4a,6,7,7a-hexahydro-5H-cyclopenta[4,5]imidazo[2,1-b]thiazole.

2,2-Dimethyl-3-[((ethoxy)(propylthio)phosphinoethioyl)oximino]-2,3-dihydro-6H-thiazolo[3,2-b][1,2,4]oxadizole.

7,7-Dichloro-2,2-dimethyl-3-[((ethoxy)(propylthio)phosphinothioyl)oximino]-2,3-dihydrothiazolo[3,2-a]pyrimidine.

6,6-Dichloro-2,2-dimethyl-3-[((ethoxy)(propylthio)phosphinothioyl)oximino]-2,3,5,6-tetrahydro-7H-thiazolo[3,2-a]pyrimidine.

2,2-Dimethyl-3-[((ethoxy)(propylthio)phosphinothioyl)oximino]-5,7-dioxo-2,3-dihydro-5H,7H-thiazolo[3,2-c]oxadiazine.

2,2-Dimethyl-5-methoxy-3-[((ethoxy)(propylthio)phosphinothioyl)oximino]-2,3-dihydroimidazo[2,1-b]thiazole.

3-[((ethoxy)(propylthio)phosphinothioyl)oximino]-2,3,5,6-tetrahydro-7H-thiazolo[3,2-a]pyrimidine.

2-Ethyl-3-[((ethoxy)(propylthio)phosphinothioyl)oximino]-2,3-dihydroimidazo[2,1-b]thiazole.

2-Trichloromethyl-3-[((ethoxy)(propylthio)phosphinothioyl)oximino]-2,3-dihydroimidazo[2,1-b]thiazole.

2-Isopropyl-3-[((ethoxy)(propylthio)phosphinothioyl)oximino]-2,3,5,6-tetrahydro-7H-thiazolo[3,2-a]pyrimidine.

2,2-Dimethyl-3-[((ethoxy)(propylthio)phosphinothioyl)oximino]-2,3-dihydroimidazo[2,1-b]thiazole-1,1-dioxide.

O-(3,5-Dimethyl-2-methylimino-5-hexyl-1,3-thiazolidin-4-ylidinimino)-O-ethyl-S-n-propylthiophosphate.

O-(3-Methyl-2-methylimino-1,3-thiazolidin-4-ylidinimino)-O-ethyl-S-n-propylphosphorodithiolate.

O-(3-n-Butyl-2-n-butylimino-5-methyl-5-n-hexyl-1,3-thiazolidin-4-ylidinimino)-O-ethyl-S-n-propylthiophosphate.

O-(3-n-Hexyl-2-n-hexylimino-5,5-dimethyl-1,3-thiazolidin-4-ylidinimino)-O-ethyl-S-n-propylthiophosphate.

O-(3-n-Butyl-2-methylimino-5,5-dimethyl-1,3-thiazolidin-4-ylidinimino)-O-ethyl-S-n-propylthiophosphate.

O-(3-Methyl-2-methylimino-5,5-dimethyl-1,3-thiazolidin-4-ylidinimino)-O-ethyl-N,N-dimethyl phosphoramidate.

O-(3-Methyl-2-methylimino-5,5-dimethyl-1,3-thiazolidin-4-ylidinimino)-O-n-plentyl-S-n-pentylthiophosphate.

O-(3-Methyl-2-methylimino-5,5-dimethyl-1,3-thiazolidin-4-ylidinimino)-O-methyl-S-methylthiophosphate.

O-(3-Methyl-2-methylimino-5,5-dimethyl-1,3-thiazolidin-4-ylidinimino)-O-ethyl-S-iso-pentylthiophosphate.

O-(3-Methyl-2-methylimino-5,5-dimethyl-1,3-thiazolidin-4-ylidinimino)-O-n-butyl-S-n-butylthiophosphate.

O-(2,3,5,6-Tetrahydro-2-methyl-2-n-pentylimidazo[2,1-b]thiazolo-3-ylidinimino)-O-ethyl-S-n-propylthiophosphate.

O-(2,3-Dihydro-2,2-dimethyl-5-S-n-propylimidazo[2,1-b]thiazolo-3-ylidinimino)-O-ethyl-S-n-propylthiophosphate.

O-(2,3-Dihydro-2,2-dimethyl-6-phenoxyimidazo[2,1-b]thiazolo-3-ylidinimino)-O-ethyl-S-n-propylthiophosphate.

O-(2,3,5,6-Tetrahydro-2,2-dimethyl-6-N,N-dimethylamine-7H-thiazolo[3,2-a]pyrimidin-3-ylidinimino)-O-ethyl-S-n-propylthiophosphate.

O-(3-Methyl-2-methylimino-5,5-dimethyl-1,3-thiazolidin-4-ylidinimino)-O-ethyl-S-methylthiomethylthiophosphate.

The phosphorous esters of this invention can be conveniently prepared from amidoximes according to either reaction method illustrated below:

METHOD I

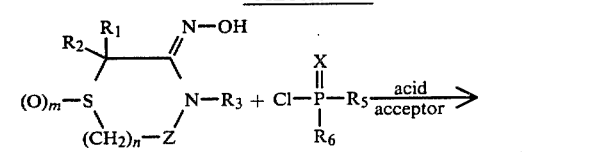

METHOD II

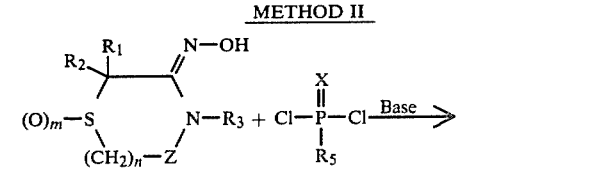

-continued

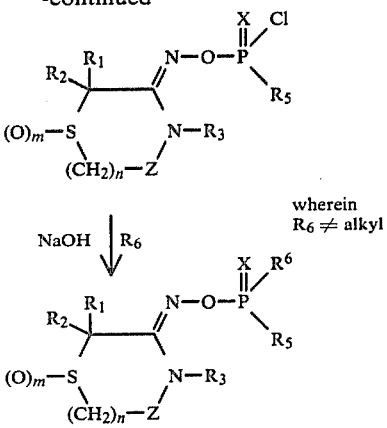

wherein $R_6 \neq$ alkyl

In the reactions illustrated in Methods I and II, one equivalent of the oxime is reacted with an appropriate mono- or dichloro phosphorus compound in the presence of at least one equivalent of an acid acceptor, preferably in an inert solvent. In Method II, as indicated, the intermediate is reacted with an appropriate alcohol, thiol or amine in the presence of one equivalent of strong base such as sodium hydroxide.

The acid acceptor utilized in Method I can be either an organic or inorganic base. Illustrative of organic bases that are useful acid acceptors include tertiary amines, such as triethylamine, pyridine, trimethylamine, or 1,4-diazobicyclo[2.2.2]octane; materials such as sodium carbonate, potassium carbonate and sodium hydroxide are illustrative of inorganic bases that are useful acid acceptors shown in Method II.

In general, most organic solvents that are inert to the reactants or reaction conditions may be employed in the Methods shown above. Illustrative of organic solvents which are generally suitable for use in conducting these reactions are aromatic hydrocarbons (optionally substituted) such as toluene, xylene, naphthlene or the like; aliphatic hydrocarbons (optionally substituted) such as methylene chloride, chloroform, carbon tetrachloride, and mono, di- and tri-chlorethylene; low boiling aliphatic ketones and nitriles such as acetone, methylethyl-, methylisopropyl-, and methylisobutyl ketone, acetonitrile and propionitrile, and ethers such as dioxane and tetrahydrofuran.

The reactions illustrated in Methods I and II can also be conducted in a solvent which functions as an acid acceptor. Illustrative of such multifunctioned solvents are N,N-dimethyl aniline, pyridine, α-picoline, any lutidine, collodine, or any like aromatic or heterocyclic tertiary amine compounds.

The reactions illustrated are neither temperature nor pressure sensitive and can be conducted over a broad temperature and pressure range to yield the desired product. Preferably, these reactions are conducted at a temperature of −40° C. to about 120° C. and at atmospheric or autogeneous pressure.

The phosphorous halides utilized as reactants in the above reaction scheme generally are known materials which can be obtained from commercial sources or prepared in accordance with conventional methods known to those skilled in the art.

In general, the bicyclic amidoximes can be conveniently prepared according to the procedure disclosed in the copending application of D. F. Bushey and T. D.

D'Silva, Ser. No. 163,631 filed June 27, 1980 concurrently herewith and which is assigned to a common assignee, the disclosure of which is incorporated by reference. Briefly, however, the oximes can be prepared by reacting a cyclic thiourea with a dichloro-oxime according to Method III below:

METHOD III

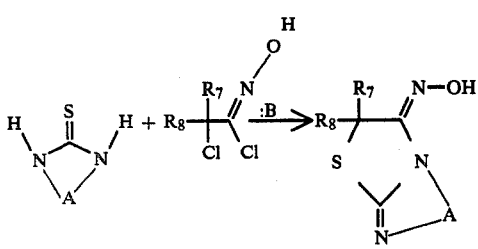

wherein $R_7$ and $R_8$ are the same or different and are individually hydrogen, $C_1$-$C_6$ alkyl or halogen; and A is a cyclic or bicyclic alkylene or alkenylene group, or an ortho-substituted phenylene group which forms an unsaturated five, six or seven membered heterocyclic ring which can also contain oxygen, sulfur, or nitrogen in addition to the two nitrogens, said alkylene, alkenylene, or phenylene ring systems being optionally substituted with one or more $C_1$-$C_4$ alkyl, alkoxy, phenoxy, alkylthio, halogen, amino, alkylamino, nitrile, carbonyl, or nitro groups.

The reaction of Method III can be conducted in aqueous or organic solvents with an appropriate acid acceptor. The reactions are preferably carried out in methanol using sodium bicarbonate as the acid acceptor. The temperature is preferably held between $-78°$ C. and $0°$ during addition of starting materials and the mixture is slowly allowed to warm to $25°$ C. The time of reaction varies between 16 hours and 3 days.

Preparation of
2,2-Dimethyl-3-hydroxyimino2,3,5,6tetrahydroimidazo[2,1-b]thiazole A 10.2 g (65.4 mmol) of 2-chlorohydroxamoyl chloride was dissolved in 200 ml of methanol and immediately cooled in an ice bath to 0°. To this solution was added 6.68 g (65.4 mmol) of 2-imidazolidinethione in one portion. After the reaction mixture was stirred at 0° for ca. 10 min., 11.09 g (132 mmol) of sodium bicarbonate was added in portions. The reaction mixture was allowed to stir at 25° C. overnight before the solvent was removed in vacuo. The residue was extracted with absolute ethanol and the ethanolic extracts were concentrated in vacuo. The residue was triturated with cold acetonitrilehexane. The insoluble solid (22%) was identified as the desired product:

mp: 188°-191°. nmr (5% DMSO-d6) 9.75 (br, 1, NOH), 4.10 (brs, 4, —N—CH$_2$CH$_2$N—), 3.50-3.30 m,4,2H$_2$O), 1.67 (s,6, gem-dimethyl). ir (CH$_2$Cl$_2$) 3570, 1670, 1620, 1200, 920 cm$^{-1}$.

The following specific examples are presented to more particularly illustrate this invention. Examples I and VIII indicate the specific procedures utilized to prepare the phosphate and phosphonate compounds respectively and these procedures were followed to prepare the applicable compounds indicated in Examples II-VII and IX-XI. Table I shows nomenclature and structure of the compounds of the Examples whereas Table II shows the physical properties.

EXAMPLE I

Preparation Of
O-(3-Methyl-2-Methylimino-5,5-Dimethyl-1,3-Thiazolidin-4-ylidinimino)O-Ethyl-S-n-Propylthiophosphate A 100 ml flask was equipped with a magnetic stirrer, condenser, drying tube and thermometer. The glassware was dried thoroughly and charged with 4.0 grams (0.0214 mole) of 2-methylimino-4-hydroxyimino-3,5,5-trimethyl-1,3-thiazolidine, 50 ml of acetonitrile and 3.3 grams (0.0246 mole) potassium carbonate. The material was stirred at 60° C. for one hour and then cooled to 40° C. To this 8.1 grams (0.040 mole) of O-ethyl-S-n-propyl thiochlorophosphate was added dropwise. The reaction mixture was then heated to 50° C. for two hours, cooled to room temperature and stirred overnight. The reaction mixture was then taken up in 100 ml of water and extracted with ethyl ether (1×200 ml), toluene (1×100 ml), and finally methylene chloride (1×50 ml). The organic layers were combined and washed quickly with 2×250 ml 8N sodium hydroxide, 2×250 ml water and the organic layer dried over anhydrous magnesium sulfate. The organic layer was then mixed with activated carbon and filtered through Celite and concentrated. The residue was then chromatographed on a low pressure liquid chromatography unit using methylene chloride/ethyl acetate to yield 2.1 grams of a viscous oil, identified as the desired product. ($n_D^{20}$ 1.5352).

Calculated for $C_{12}H_{24}N_3O_3PS_2$: C, 40.79; H, 6.80; Found: C, 40.93; H, 6.93.

EXAMPLE VIII

Preparation of
O-Ethyl-P-Ethyl-O-(2,3,5,6-Tetrahydro-2,2-Dimethyl-7H-Thiazolo[3,2-a]Pyrimidin-3-ylidinimino)Thionophosphonate A 920 mg (21 mmol) quantity of sodium hydride (55% mineral oil dispersion) was washed twice with dry tetrahydrofuran and then 100 ml of dry tetrahydrofuran was added to the sodium hydride. To the tetrahydrofuran mixture was added 4.0 gram (20.1 mmol) of 2,2-dimethyl-3-hydroxyimino-2,3,5,6-tetrahydro-7H-thiazolo[3,2-a]pyrimidine as a slurry in 50 ml dry tetrahydrofuran. The mixture was then heated (while stirring) to 60° C. for one hour at which time it was cooled to 30° C.

3.47 Gram (20.1 mmol) of O-ethyl-ethyl phosphonochloridate dissolved in 10 ml dry tetrahydrofuran was added dropwise and the mixture stirred overnight at room temperature.

The mixture was filtered through Celite and concentrated. The residual oil was dissolved in 150 ml methylene chloride and washed with 2N sodium hydroxide (2×150 ml), water (2×150 ml) and then dried over anhydrous magnesium sulfate and filtered. The resulting solution was concentrated to yield an oil which was then eluted through a low pressure liquid chromatography with chloroform/ethyl acetate to yield 3.76 grams of the desired product.

Calculated for $C_{12}H_{22}N_3O_2PS_2$: C, 42.97; H, 6.61; Found: C, 43.09; H, 6.71.

TABLE I

| Example | Nomenclature | Structure |
|---|---|---|
| II | O—(3-Methyl-2-methylimino-5,5 dimethyl-1,3-thiazolidin-4-ylidinimino)-O—ethyl-S—n-propylidithiophosphate | 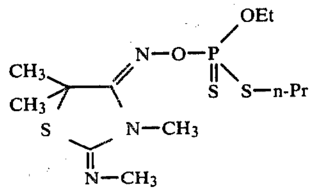 |
| III | O—(3-Ethyl-2-ethylimino-5,5-dimethyl-1,3-thiazolindin-4-ylidinimino)-O—ethyl-S—n-propylthiophosphate | 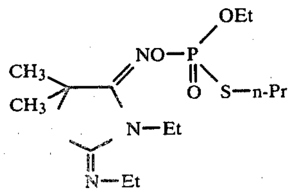 |
| IV | O—(3-Ethyl-2-ethylimino-5,5-dimethyl-1,3-thiazolidin-4-ylidinimino)-O—ethyl-S—n-propylphosphorodithioate | 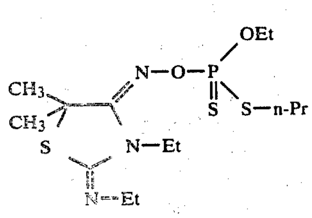 |
| V | O—(3-Isopropyl-2-isopropylimino-5,5-dimethyl-1,3-thiazolidin-4-ylidinimino)-O—ethyl-S—n-propylthiophosphate | 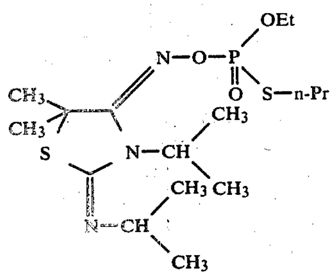 |
| VI | O—(3-isopropyl-2-isopropylimino-5,5-dimethyl-1,3-thiazolidin-4-ylidinimino)-O—ethyl-S—n-propylphosphorodithioate | 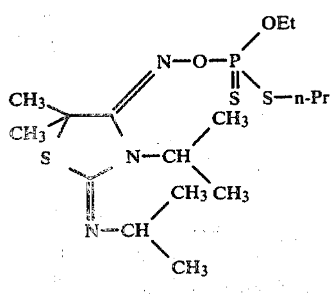 |
| VII | O—(2,3,5,6-Tetrahydro-2,2-dimethyl-7H-thiazolo[3,2-a]pyrimidin-3-ylidinimino)-O—ethyl-S—n-propylthiophosphate | 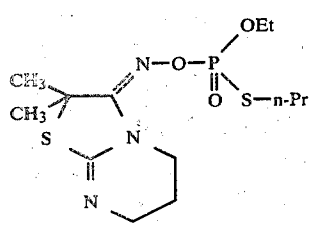 |
| IX | O—(2,3,5,6-Tetrahydro-2,2-dimethylimidazo[2,1-b]thiazol-3-ylidinimino)-O—ethyl-S—n-propylphosphorodithioate | 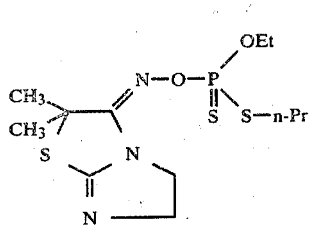 |

TABLE I-continued

| Example | Nomenclature | Structure |
|---------|-------------|-----------|
| X | O—(2,3-Dihydro-2,2-dimethylimidazo[2,1-b]thiazol-3-ylidinimino)-O—ethyl-S—n-propylphosphorodithioate | 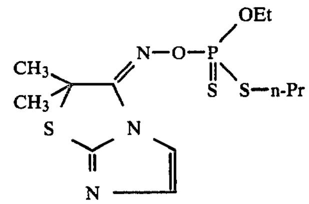 |
| XI | O—(2,2-Dimethyl-1,4-thiomorpholinyl-3-hydroxyimino)-O—ethyl-S—n-propylthiophosphate | 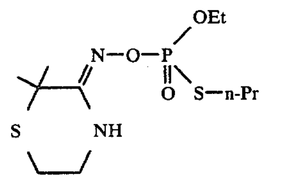 |

TABLE II

| Example | Refractive Index (°C.) | Molecular Formula | Elementary Analysis Calc. | Found |
|---------|------------------------|-------------------|---------------------------|-------|
| II | — | $C_{12}H_{24}N_3O_2PS_3$ | C, 39.00<br>H, 6.55 | C, 39.85<br>H, 6.50 |
| III | — | $C_{14}H_{28}N_3O_3PS_2$ | C, 44.08<br>H, 7.40 | C, 42.61<br>H, 7.50 |
| IV | — | $C_{14}H_{28}N_3O_2PS_3$ | C, 42.29<br>H, 7.10 | C, 42.84<br>H, 7.21 |
| V | 1.5078(23) | $C_{16}H_{32}N_3O_3PS_2$ | C, 46.92<br>H, 7.88 | C, 46.36<br>H, 8.20 |
| VI | 1.5285(22) | $C_{16}H_{32}N_3O_2PS_3$ | C, 45.15<br>H, 7.58 | C, 44.13<br>H, 7.36 |
| VII | — | $C_{13}H_{24}N_3O_3PS_2$ | C, 42.72<br>H, 6.62 | C, 42.85<br>H, 6.60 |
| IX | — | $C_{12}H_{22}N_3O_2PS_3$ | C, 39.22<br>H, 6.03 | C, 38.76<br>H, 5.80 |
| X | — | $C_{12}H_{20}N_3O_2PS_3$ | C, 39.43<br>H, 5.52 | C, 39.81<br>H, 5.53 |
| XI | — | $C_{11}H_{23}N_2O_3PS_2$ | C, 40.47<br>H, 7.10 | C, 39.36<br>H, 6.96 |

Selected new compounds were evaluated to determine their pesticidal activity against mites, and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylaryl polyether alcohol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described below were obtained by appropriate dilutions of the stock suspension with water. The test procedures were as follows:

Adults and nymphal stages of the bean aphid (*Aphis fabae* Scop.) reared on potted dwarf nasturtium plants at 65°–70° F. and 50±5 percent relative humidity, constituted with test insects. For testing purposes, the number of aphids per pot was standarized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test comound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead.

Larvae of the southern armyworm (Spodopteraeridania, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead.

Fourth instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5 F. for three days. Although the larvae could easily consume the leaf within 24 to 48 hours, no more food was added. Larvae which were unable to move the length of the body, even upon stimulation, were considered dead.

Four to six day old adult house flies (*Musca domestica*, L.), reared according to the specifications of the Chemical Specialties Manufacturing Association (Blue Book, McNair-Dorland Co., N.Y. 1954; pages 243-244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Adults and nymphal stages of the two-spotted mite (*Tetranychus urticae* (Koch)), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of water solution containing acetone and emulsifier in the same concentration as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table III below. In these tests the pesticidal activity of the compounds at the indicated dosage rate against aphid, mite, Southern Armyworm, Bean Beetle and house fly was rated as follows:

A=excellent control
B=partial control
C=no control

TABLE III

| | Biological Activity | | | | | |
|---|---|---|---|---|---|---|
| Example | Bean Aphid | Mite Adult | Mite Egg | Southern Armyworm | Mexican Bean Beetle | House Fly |
| I | A | A | B | A | A | A |
| II | A | A | C | A | A | A |
| III | A | A | C | A | A | A |
| IV | A | A | C | A | A | A |
| V | A | A | C | A | A | A |
| VI | A | A | A | A | A | A |
| VII | A | A | C | A | A | A |
| VIII | A | A | C | B | C | A |
| IX | B | A | C | A | B | A |
| X | A | A | C | A | C | A |
| XI | B | A | C | B | B | A |

It will be understood that the plant species employed in the above tests are merely representative of a wide variety of plant pest that can be controlled by the use of the compounds of this invention. The compounds contemplated in this invention may be applied as mite ovicides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not reemulsify the toxicant after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when 12. A composition according to claim 11 wherein $R_3$ and $R_4$ are both methyl.

13. A composition according to claim 11 wherein $R_3$ and $R_4$ are both ethyl.

14. A composition according to claim 11 wherein the active toxicant is O-(3-Methyl-2-methylimino-5,5-dimethyl-1,3-thiazolidin-4-ylidinimino)-O-ethyl-S-n-propylthiophosphate.

15. A composition according to claim 11 wherein the active toxicant is O-(3-Methyl-2-methylimino-5,5-dimethyl-1,3-thiazolidin-4-ylidinimino)-O-ethyl-S-n-propyldithiophosphate.

16. A composition according to claim 11 wherein the active toxicant is O-(3-Ethyl-2-ethylimino-5,5-dimethyl-1,3-thiazolidin-4-ylidinimino)-O-ethyl-S-n-propylthiophosphate.

17. A composition according to claim 11 wherein the active toxicant is O-(3-Ethyl-2-ethylimino-5,5-dimethyl-1,3-thiazolidin-4-ylidinimino)-O-ethyl-S-n-propylphosphorodithioate.

18. A composition according to claim 11 wherein the active toxicant is O-(2,3,5,6-tetrahydro-2,2-dimethyl-7H-thiazolo[3,2-a]pyrimidin-3-ylidinimino)-O-ethyl-S-n-propylthiophosphate.

19. A method of controlling insects which comprises subjecting them to an insecticidally effective amount of a compound of the formula:

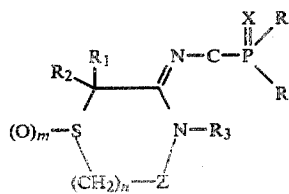

wherein
m is 0, 1 or 2;
n is 0 or 1;
X is O or S;
$R_1$ and $R_2$ can be the same or different and are hydrogen or $C_1$ to $C_6$ alkyl; with the proviso that when n is 0, Z is C=N—$R_4$; and when n is 1, Z is $CH_2$ and $R_3$ is hydrogen or lower alkyl;

$R_3$ and $R_4$ can be the same or different and is lower alkyl ($C_1$-$C_6$) or together forms a cyclic alkylene or alkenylene group thereby forming a five or six membered ring which can also have nitrogen, or carbonyl, in addition to the two nitrogens said alkylene or alkylene ring systems being optionally substituted with one or two $C_1$ to $C_4$ alkyl, cyclohexyl, halogen, nitrile, or nitro groups;

$R_5$ and $R_6$ is the same or different and is $C_1$ to $C_6$ alkyl, $C_1$ to $C_5$ alkoxy, $C_1$ to $C_5$ alkylthio, alkylthioalkyl, dialkylamino, or alkylamino.

20. A method according to claim 19 wherein:
m is 0,
n is 0,
x is oxygen or sulfur
Z is C=N—$R_4$
$R_1$ and $R_2$ are methyl, and
$R_3$ and $R_4$ are both lower alkyl.

21. A method according to claim 20 wherein:
$R_3$ and $R_4$ are both methyl.

22. A method according to claim 20 wherein $R_3$ and $R_4$ are both ethyl.

23. A method according to claim 19 wherein the compound is O-(3-Methyl-2-methylimino-5,5-dimethyl-1,3-thiazolidin-4-ylidinimino)-O-ethyl-S-n-propylthiophosphate.

24. A method according to claim 19 wherein the compound is O-(3-Methyl-2-methylimino-5,5-dimethyl-1,3-thiazolidin-4-ylidinimino)-O-ethyl-S-n-propyldithiophosphate.

25. A method according to claim 19 wherein the compound is O-(3-Ethyl-2-ethylimino-5,5-dimethyl-1,3-thiazolidin-4-ylidinimino)-O-ethyl-S-n-propylthiophosphate.

26. A method according to claim 19 wherein the compound is O-(3-Ethyl-2-ethylimino-5,5-dimethyl-1,3-thiazolidin-4-ylidinimino)-O-ethyl-S-n-propylphosphorodithioate.

27. A method according to claim 19 wherein the compound is O-(2,3,5,6-tetrahydro-2,2-dimethyl-7H-thiazolo[3,2-a]pyrimidin-3-ylidinimino)-O-ethyl-S-n-propylthiophosphate.

* * * * *

UNITED STATES PATENT AND TRADEMARK OFFICE
CERTIFICATE OF CORRECTION

PATENT NO. : 4,479,946

DATED : October 30, 1984

INVENTOR(S) : Leonard E. Hodakowski et al.

It is certified that error appears in the above-identified patent and that said Letters Patent is hereby corrected as shown below:

In the claims, claim 1, that portion reading

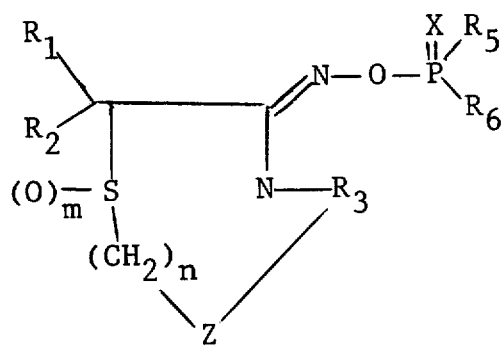

UNITED STATES PATENT AND TRADEMARK OFFICE
CERTIFICATE OF CORRECTION

PATENT NO. : 4,479,946  Page 2 of 2
DATED : October 30, 1984
INVENTOR(S) : Leonard E. Hodakowski et al.

It is certified that error appears in the above-identified patent and that said Letters Patent is hereby corrected as shown below:

should read

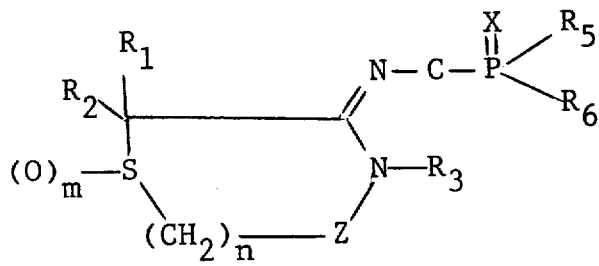

Signed and Sealed this

Sixteenth Day of July 1985

[SEAL]

Attest:

DONALD J. QUIGG

Attesting Officer   Acting Commissioner of Patents and Trademarks